United States Patent
Devine, II

(10) Patent No.: US 6,524,395 B1
(45) Date of Patent: Feb. 25, 2003

(54) METHOD AND APPARATUS FOR LOCATING AND REPAIRING COOLING ORIFICES OF AIRFOILS

(75) Inventor: Robert Henry Devine, II, Simpsonville, SC (US)

(73) Assignee: General Electric Company, Schenectady, NY (US)

( * ) Notice: Subject to any disclaimer, the term of this patent is extended or adjusted under 35 U.S.C. 154(b) by 1 day.

(21) Appl. No.: 09/956,927

(22) Filed: Sep. 21, 2001

(51) Int. Cl.⁷ ................................................. B08B 7/04
(52) U.S. Cl. .......................... 134/18; 134/8; 134/22.1; 134/22.12; 134/198; 29/889.1; 427/142
(58) Field of Search ............................. 134/2, 8, 6, 18, 134/22.1, 22.18, 22.12, 34, 56 R, 58 R, 166 R, 168 R, 168 C, 167 C, 169 R, 166 C, 172, 173, 174, 198; 29/889.1; 415/178; 204/279; 427/142

(56) References Cited

U.S. PATENT DOCUMENTS

| | | | |
|---|---|---|---|
| 5,216,808 A | * | 6/1993 | Martus et al. ............. 29/889.1 |
| 5,222,617 A | | 6/1993 | Gregory et al. |
| 5,643,474 A | | 7/1997 | Sangeeta |
| 5,941,686 A | * | 8/1999 | Gupta et al. ................. 415/178 |
| 6,004,620 A | * | 12/1999 | Camm ......................... 427/142 |
| 6,238,743 B1 | | 5/2001 | Brooks |
| 6,258,226 B1 | * | 7/2001 | Conner ....................... 204/279 |
| 6,267,902 B1 | | 7/2001 | Cartier et al. |

* cited by examiner

Primary Examiner—Randy Gulakowski
Assistant Examiner—Gentle Winter
(74) Attorney, Agent, or Firm—Nixon & Vanderhye

(57) ABSTRACT

An apparatus for identifying and clearing blockages in cooling orifices of an airfoil is described. The apparatus includes a processor for controlling the various functions of the apparatus. Light is directed into a cavity of the airfoil and a detector is used for detecting light passing through the orifices. The processor determines blockages of the orifices by comparing detected light pattern with a predetermined pattern. The apparatus further includes a nozzle controlled by the processor for directing pressurized water to open the blocked orifices.

15 Claims, 3 Drawing Sheets

METHOD AND APPARATUS FOR LOCATING AND REPAIRING COOLING ORIFICES OF AIRFOILS

This invention relates to airfoils, and more particularly to a method and apparatus for locating and repairing closed cooling holes of airfoils after strip and recoat in DVC thermal barrier coating (TBC) applications.

BACKGROUND OF THE INVENTION

Thermal-barrier coatings are increasingly applied to hot components in gas turbines, and the most prominent application processes are plasma spraying and electron-beam physical vapor deposition. Electron-beam physical vapor deposition provides distinctive coatings of a unique columnar microstructure. The main advantage of this structure is its superior tolerance against straining and erosion, thus giving it a major edge in lifetime. Furthermore, cooling hole closure will be prevented and an aerodynamic design of the blades is maintained. However, in power systems, the DVC TBC is a plasma type process, therefore the issue of coat down still exits.

Blades and vanes of a high-pressure turbine section of aeroengines are among the most highly stressed parts in engineering components. Internally cooled airfoils of state-of-the-art nickel-based superalloys operate at temperatures of about 1,000° C. with short-term peaks above 1,100° C., which is close to 90% of the alloys' melting points.

This high gas-turbine inlet temperature can only be maintained through uneconomical advanced cooling techniques or by the introduction of electron-beam physical vapor deposition (EB-PVD) thermal-barrier coatings (TBCs). Such TBCs consist of thin ceramic layers of low thermal conductivity, such as partially stabilized zirconia (PSZ) that are applied on airfoil surfaces having a metallic corrosion-resistant coating. The coating imparts good adhesion of the ceramic to the substrate. The application of the TBCs increases the engine performance by either increasing the gas-turbine inlet temperature or reducing the required cooling-air flow. Alternatively, the lifetime of the turbine blades can be extended by decreasing metal temperatures.

Plasma-sprayed (PS) TBCs have been widely applied to hot components like burner cans since the 1960s, while in recent applications of more complex parts like turbine blades, EB-PVD technology is favored. During EB-PVD, a high-energy EB melts and evaporates a ceramic-source ingot in a vacuum chamber. Preheated substrates are positioned in the vapor cloud above a point where the vapor is deposited on substrates at deposition rates of 0.1–0.25 mm/s. Typical columnar microstructures and aerodynamically smooth surfaces are obtained without the need for final polishing or conditioning of cooling holes. Due to the columnar microstructure, the lifetime of the TBCs is prolonged and the damage tolerance improved.

Turbine blades in high performance gas turbine engines are frequently subjected to working temperatures near or even above the melting point of the alloy of which the blades are made. In order to maintain the integrity of the blades under working conditions, it is now common practice to provide cavities within the blades and holes from the cavities to the exteriors of the blades, both to surfaces and edges. Cooling air is directed from the cavities through the holes over the surfaces and edges. The number, shape, disposition and size of the holes are parameters which are essential to the efficient cooling of the blades by this method.

Repairing airfoils includes stripping and recoating the thermal barrier coatings (TBC) of the airfoil related to a hot gas component, such as for example, turbine nozzles, buckets, and shrouds. Because of the modern advanced cooling schemes that are being used to cool airfoils in order to meet performance in the field, smaller and shaped cooling holes are required to meet film distribution parameters for cooling the airfoils. These smaller holes are susceptible to closure from the application of new coatings that are applied after repairs are made. Thus, cooling holes are greatly reduced in diameter thereby creating insufficient film cooling. Thus, there is a need to identify closed or reduced diameter cooling holes and clear the openings to improve machine life.

BRIEF SUMMARY OF THE INVENTION

Accordingly, the present invention relates to a method and apparatus for determining the reduction in openings of cooling holes of airfoils, and rectify the problem by forcing jets of water to clear the TBC deposits from the cooling holes.

This is achieved by directing a source of light into an airfoil cavity and detecting the light through the cooling holes of the airfoil using a detector. Since the coordinates of cooling holes are determined and known apriori, the light passing through a hole produces a predictable pattern. In the event of not receiving a predetermined pattern of light from a select hole, it is deduced that there might be a reduction in the cooling hole diameter. Upon identifying a clogged cooling hole due to the deposition of TBC coating, waterjets are used to drill down a determined vector and open the hole by eroding away the TBC that has been redeposited as a result of airfoil repair.

In its broader aspects, the present invention provides a method of cleaning cooling orifices of an airfoil, said method comprising: directing a light source into airfoil cavity; detecting and measuring light passing through the orifices; comparing the measured light with predetermined light pattern for the airfoil; identifying blocked orifices from the comparison step; and clearing the blocked orifices. The step of clearing the blocked orifices further includes determining the coordinates of the blocked orifices; causing a nozzle to move to selected coordinates; and forcing pressurized water through the nozzle to clear the blockage. The method further includes controlling the nozzle by a processor system.

In another aspect, a method of identifying and clearing cooling hole blockages of an airfoil coated with thermal barrier coatings, the method includes directing a light source into an airfoil cavity; detecting light passing through cooling holes of the airfoil; comparing the detected light with predetermined light pattern; identifying closed or partially blocked cooling holes from the comparison step; and clearing the closed or partially blocked cooling holes by forcing water through the closed or partially blocked cooling holes.

In yet another aspect, an apparatus for cleaning cooling orifices of an airfoil, comprising means for directing a light source into airfoil cavity; means for detecting and measuring light passing through the orifices; means for comparing the measured light with predetermined light pattern for the airfoil; means for identifying blocked orifices from the comparison step; and means for clearing the blocked orifices by pressurized water.

In a further aspect, the present invention is an apparatus for identifying and clearing blockages in cooling orifices of an airfoil, comprising: a processor for controlling the various functions of the apparatus; a light source for directing light into a cavity of the airfoil; a detector for detecting light passing through the orifices, said processor determining blockages of the orifices by comparing detected light pattern with a predetermined pattern; and a nozzle controlled by the processor for directing pressurized water to open the blocked orifices. The processor preferably includes a database for storing orifice configurations of the airfoil. The processor further includes a comparator for comparing the measured light pattern with predetermined light pattern for a select airfoil. The light source and detector are preferably controlled by the processor. The processor system further comprises a display interface.

In yet another aspect, a method for identifying and clearing blockages in cooling orifices of an airfoil, the method comprising controlling the various functions of the apparatus using a processor system; directing light into a cavity of the airfoil; detecting light passing through the orifices; determining blockages of the orifices by comparing detected light pattern with a predetermined pattern; and directing pressurized water to open the blocked orifices.

DETAILED DESCRIPTION OF THE INVENTION

Figure 1:
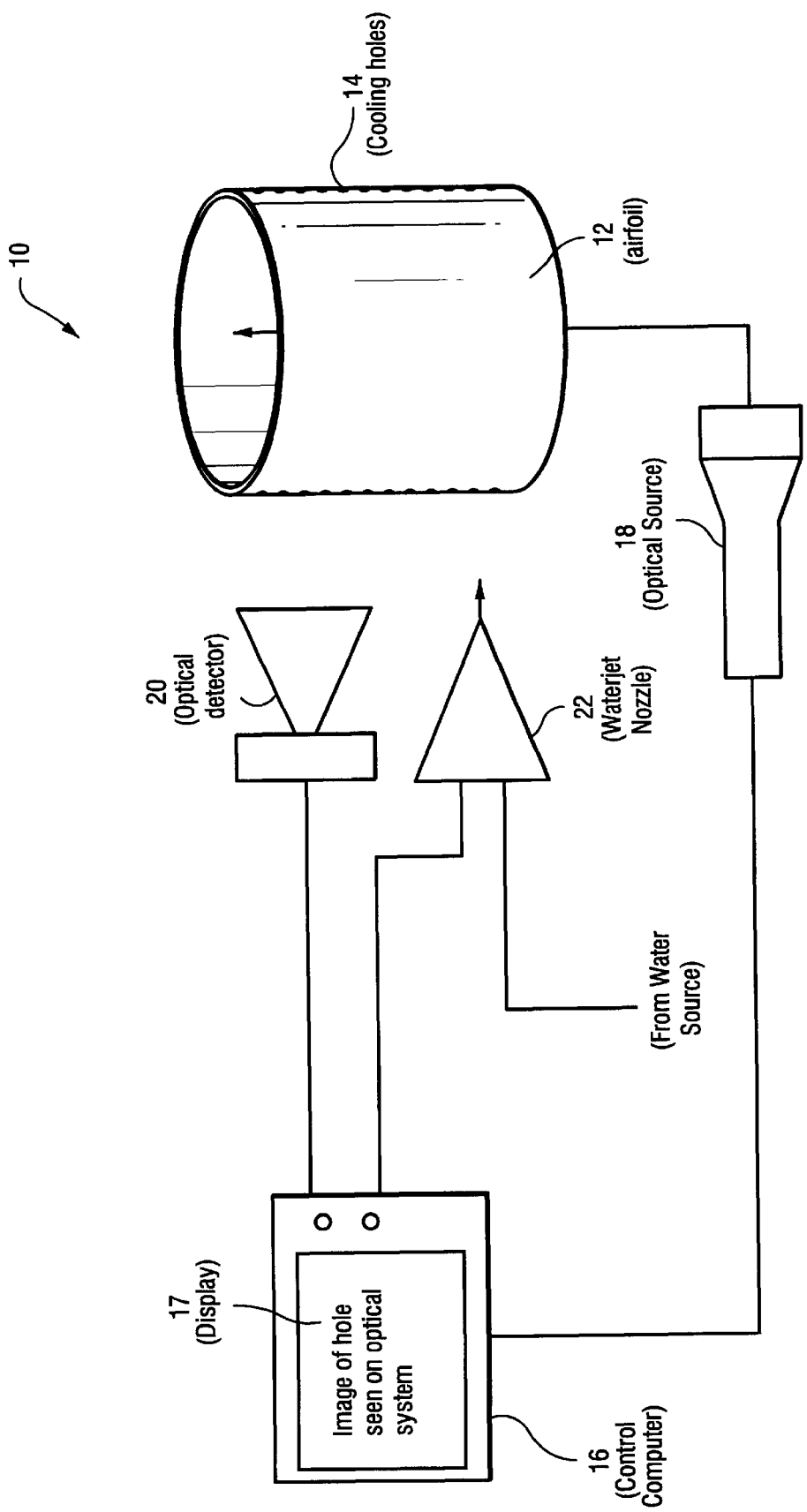
FIG. 1 illustrates a schematic for identifying and clearing blocked orifices of an airfoil in accordance with an exemplary embodiment of the present invention.

FIG. 1 shows a schematic for identifying and clearing blocked orifices/cooling holes of an airfoil. The exemplary schematic includes an optical source 18, an optical detector system 20, a control computer 16 with a display 17, and a waterjet nozzle 22 coupled to a water source (not shown). The movement of nozzle 22 is controlled by control computer 16.

In operation, light from the light source 18 is projected into a cavity of airfoil 12 such that projected light passes through cooling holes 14 of the airfoil to be detected by the optical detector 20. Cooling holes that are blocked or partially blocked due to TBC coating/deposits fail to permit light through the holes and as a result, the detector 20 fails to detect the blocked holes. For each airfoil type in good condition (i.e., without cooling hole blockages), the light pattern produced by passing light through the cooling holes is predetermined and stored in the control computer 16. The coordinates of the cooling holes are also predetermined and correlated with the predetermined light pattern. The coordinates with correlated light pattern are stored in the control computer 16. Measured light pattern from the subject airfoil 12 is compared with the predetermined light pattern of an airfoil having similar characteristics in order to determine blocked cooling holes. The coordinates of the blocked holes are determined by correlating the measured light pattern with the predetermined light pattern.

Upon obtaining the coordinates of blocked cooling holes, the waterjet nozzle 22 is moved into position by the control computer 16—the position matching the coordinates of a blocked cooling hole. The waterjet nozzle 22 is then activated to force pressurized water from a source (not shown) in order to drill down the blockage, thus clearing the blocked hole.

Figure 2:
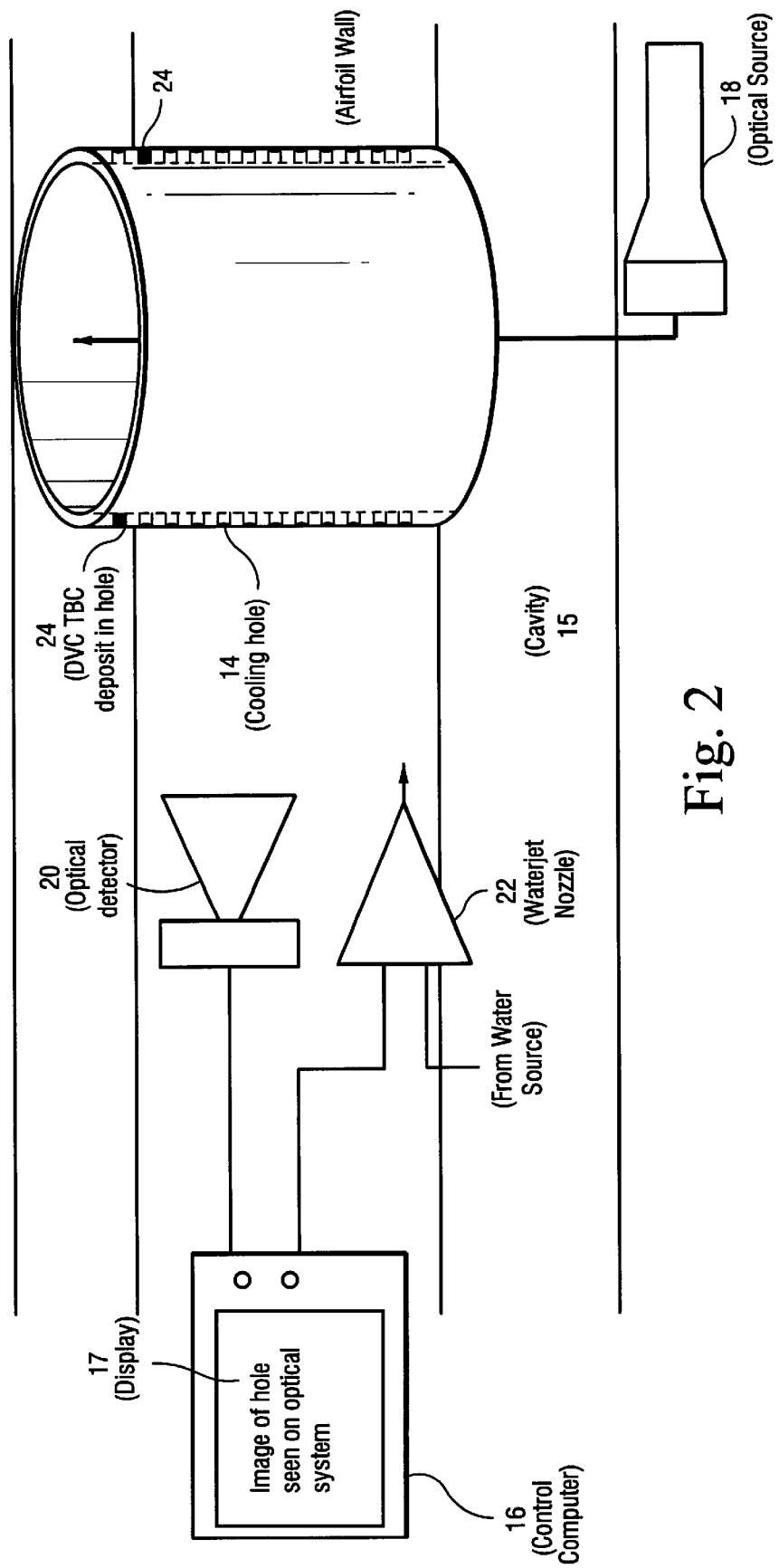
FIG. 2 illustrates detailed view of an orifice of the airfoil shown in FIG. 1 and also the TBC deposits on the inside surface of the orifice.

FIG. 2 illustrates detailed view of an orifice of the airfoil as shown in FIG. 1 and also the TBC deposits on the inside surface of the orifice. Specifically, FIG. 2 shows a detailed view identifying TBC coatings 24 partially blocking a cooling hole 14. An image of a cooling hole may be conveniently observed on a display 17 of the control computer 16 to ensure that drilling using nozzle jet and directing pressurized water into the blocked hole clears the hole of TBC deposits.

Figure 3:
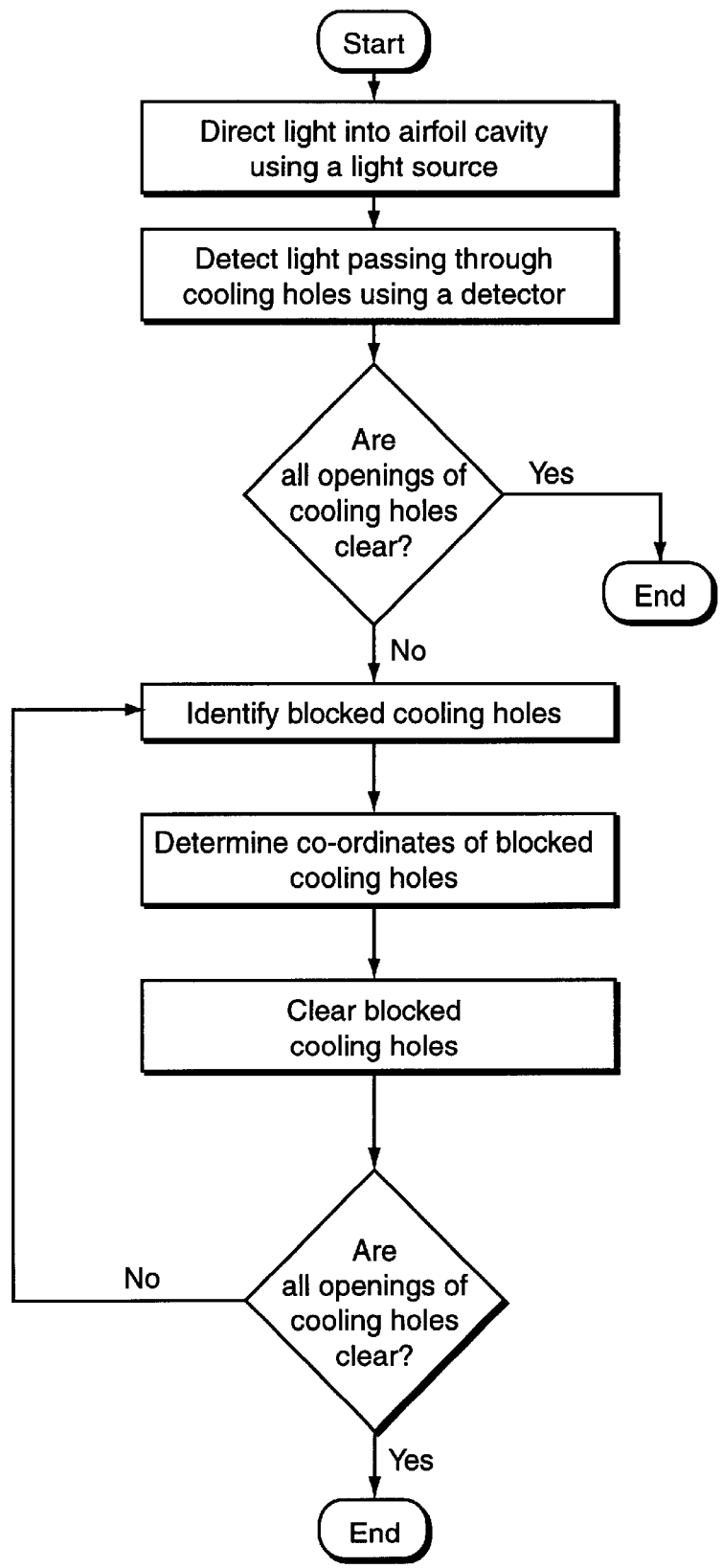
FIG. 3 illustrates a flow chart identifying the process steps for determining and clearing orifice blockages of the airfoil shown in FIG. 1.

FIG. 3 illustrates a flow chart identifying the process steps for determining and clearing orifice blockages of the airfoil shown in FIG. 1, the operation of which is set forth above and is therefore not repeated.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A method of cleaning cooling orifices of an airfoil, said method comprising:

directing a light source into airfoil cavity;

detecting and measuring light passing through the orifices;

comparing the measured light with predetermined light pattern for the airfoil;

identifying blocked orifices from the comparison step; and clearing the blocked orifices.

2. The method as in claim 1, wherein the step of clearing the blocked orifices further comprising:

determining the coordinates of the blocked orifices;

causing a nozzle to move to selected coordinates; and forcing pressurized water through the nozzle to clear the blockage.

3. The method as in claim 2, further comprising:

controlling said nozzle by a processor system.

4. A method of identifying and clearing cooling hole blockages of an airfoil coated with thermal barrier coatings, said method comprising:

directing a light source into an airfoil cavity;

detecting light passing through cooling holes of the airfoil;

comparing the detected light with predetermined light pattern;

identifying closed or partially blocked cooling holes from the comparison step; and clearing the closed or partially blocked cooling holes by forcing water through the closed or partially blocked cooling holes.

5. The method as in claim 4, wherein said water is forced using a nozzle.

6. The method as in claim 4, wherein the step of clearing the blocked orifices further comprising:

determining the coordinates of the closed or partially blocked orifices;

causing a nozzle to move to select coordinates; and forcing water through the nozzle to clear the blockage.

7. The method as in claim 6, further comprising:

controlling said nozzle by a processor system.

8. An apparatus for cleaning cooling orifices of an airfoil, comprising:

means for directing a light source into airfoil cavity;

means for detecting and measuring light passing through the orifices;

means for comparing the measured light with predetermined light pattern for the airfoil;

means for identifying blocked orifices from the comparison step; and means for clearing the blocked orifices by pressurized water.

9. An apparatus for identifying and clearing blockages in cooling orifices of an airfoil, comprising:

a processor for controlling the various functions of the apparatus;

a light source for directing light into a cavity of the airfoil;

a detector for detecting light passing through the orifices, said processor determining blockages of the orifices by comparing detected light pattern with a predetermined pattern; and a nozzle controlled by the processor for directing pressurized water to open the blocked orifices.

10. The apparatus as in claim 9, wherein said processor includes a database for storing orifice configurations of the airfoil.

11. The apparatus as in claim 9, wherein said processor further includes a comparator for comparing the measured light pattern with predetermined light pattern for a select airfoil.

12. The apparatus as in as in claim 9, wherein said light source and detector are controlled by said processor.

13. The apparatus as in claim 9, wherein said processor system further comprises a display interface.

14. The apparatus as claim 9, wherein said blockages are caused by thermal barrier coatings coated on said airfoil.

15. A method for identifying and clearing blockages in cooling orifices of an airfoil, said method comprising:

controlling the various functions of the apparatus using a processor system;

directing light into a cavity of the airfoil;

detecting light passing through the orifices;

determining blockages of the orifices by comparing detected light pattern with a predetermined pattern; and directing pressurized water to open the blocked orifices.

\* \* \* \* \*